United States Patent

Nardi et al.

[11] Patent Number: 4,507,308
[45] Date of Patent: Mar. 26, 1985

[54] ANALGESICALLY OR ANTI-INFLAMMATORY EFFECTIVE 4-QUINOLYL ANTHRANILIC ACID DERIVATIVES

[75] Inventors: Dante Nardi; Gianni Motta; Rodolfo Testa; Gabriele Graziani; Silvano Casadio, all of Milan, Italy

[73] Assignee: Recordati S.A., Chiasso, Switzerland

[21] Appl. No.: 426,229

[22] Filed: Sep. 28, 1982

[30] Foreign Application Priority Data

Sep. 30, 1981 [GB] United Kingdom ............... 8129473

[51] Int. Cl.³ .................... A61K 31/47; C07D 215/44
[52] U.S. Cl. ...................... 514/313; 546/161
[58] Field of Search ............ 424/258; 546/161

[56] References Cited

U.S. PATENT DOCUMENTS 3,479,360 11/1969 Allais et al. ............ 424/258 X
3,637,710 1/1972 Wasley et al. ........... 424/258 X
3,764,603 10/1973 Teriault et al. .......... 424/258 X

FOREIGN PATENT DOCUMENTS 0005232 8/1967 France ................... 424/258

*Primary Examiner*—Donald G. Daus
*Assistant Examiner*—Diana G. Rivers
*Attorney, Agent, or Firm*—Burns, Doane, Swecker & Mathis

[57] ABSTRACT

The novel anthranilic acid derivatives having the structural formula (I):

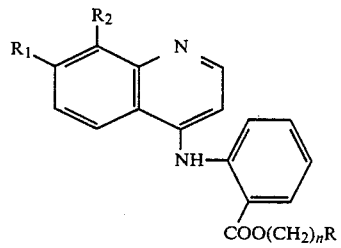

wherein n is 0, 1 or 2, one of $R_1$ and $R_2$ is chloro or trifluoromethyl and the other is hydrogen, and R is 2-oxo-3-oxolanyl or 2-oxo-3-oxazolidinyl, are effective analgesics and anti-inflammatories.

10 Claims, No Drawings

ANALGESICALLY OR ANTI-INFLAMMATORY EFFECTIVE 4-QUINOLYL ANTHRANILIC ACID DERIVATIVES

FIELD AND SUMMARY OF THE INVENTION

The present invention relates to novel analgesically and anti-inflammatory effective derivatives of anthranilic acid, to a process for the preparation thereof, and to a variety of pharmaceutical compositions comprising same.

The novel derivatives of anthranilic acid according to this invention have the structural formula (I):

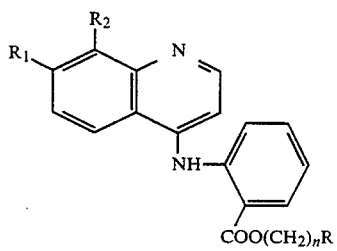

wherein n is 0, 1 or 2, one of $R_1$ and $R_2$ represents a chlorine atom or a trifluoromethyl group and the other represents a hydrogen atom, and R represents a 2-oxo-3-oxolanyl or 2-oxo-3-oxazolidinyl group.

DETAILED DESCRIPTION OF THE INVENTION

More particularly according to this invention, the subject novel compounds have been found to exhibit good analgesic and anti-inflammatory properties.

This invention also provides a process for the preparation of the compounds having the structural formula (I) as above-defined, such process comprising condensing a salt of an N-(7- or 8-substituted-4-quinolyl)-anthranilic acid having the structural formula (II):

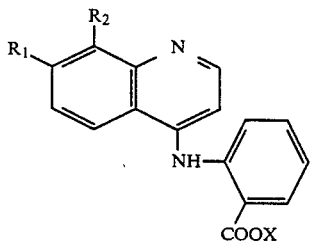

wherein $R_1$ and $R_2$ are as above-defined and X represents an alkali metal, with a halo derivative having the general formula (III):

Halo—$(CH_2)_n$—R     (III)

in which n and R are also as above-defined.

The N-(7- or 8-substituted-4-quinolyl)-anthranilic acid salt is preferably the sodium salt (II, X=Na), whereas the halo in the formula (III) is typically chlorine or bromine.

The condensation is preferably carried out in the presence of an inert inorganic solvent, such as dimethylformamide. The reactants are typically employed in equimolar proportions, with the temperature of reaction ranging from 30° to 150° C.

This invention additionally provides for eliciting an analgesic and/or anti-inflammatory response in a warm-blooded animal in need of such treatment, as well as a variety of pharmaceutical compositions comprising a compound having the structural formula (I) as above-defined in admixture with a pharmaceutically acceptable diluent or carrier therefor. Suitable such diluents or carriers and unit dosage amounts will be apparent to those skilled in this art. Compare, for example, *Remington's Pharmaceutical Sciences*, 4th Edition (1970).

The active compounds according to the invention exhibit good analgesic and anti-inflammatory activity, while at the same time displaying but low toxicity. The $LD_{50}$ values thereof, determined in the mouse both i.p. and per os, are respectively greater than 1000 and 3000 mg/Kg. This is valid for all of the novel compounds provided hereby.

The analgesic activities ($ED_{50}$), determined in the mouse utilizing the writhing test [Sigmund et al., *Proc. Soc. Exp. Biol. Med.*, 95, 729 (1957)] were found to range from 6 to 18 mg/KG. The $ED_{50}$ values for the anti-inflammatory activity were found to range from 20 to 30 mg/KG.

In order to further illustrate the present invention and the advantages thereof, the following specific examples are given, it being understood that same are intended as illustrative and in nowise limitative.

EXAMPLE 2

A mixture comprising 6.4 g of N-(7-chloro-4-quinolyl)-anthranilic acid sodium salt and 3.28 g of 3-bromo-oxolan-2-one in 40 ml of dimethylformamide was heated under stirring at 40°–45° C. for five hours. Upon completion of the reaction, the solution thus obtained was filtered and poured into 250 ml of water. The solid which precipitated was collected on a filter and treated with about 100 ml of chloroform. The entire mass was filtered again and, adding petroleum ether, N-(7-chloro-4-quinolyl)-anthranilic acid γ-butyrolactone ester was obtained. The product was collected and crystallized from isopropanol. Yield, 4 g; mp 155°–157° C.

EXAMPLE 2

A mixture comprising 12.8 g of N-(7-chloro-4-quinolyl)-anthranilic acid sodium salt, 6.64 g of 90% 3-(β-chloroethyl)-oxazolidine-2-one and 80 ml of dimethylformamide was heated under stirring at 120° C. for five hours. Upon completion of the reaction, the mixture was cooled, filtered, and the solvent eliminated in vacuo. To the residue, 80 ml of ether were added and the solid thus obtained was collected on filter and purified by chromatography on a silica gel column using ethyl acetate as eluent. The desired product was crystallized from isopropanol to give 11.2 g of N-(7-chloro-4-quinolyl)-anthranilic acid β-(2-oxo-3-oxazolidinyl)-ethyl ester, melting at 122°–124° C.

EXAMPLE 3

A mixture comprising 10.62 g of N-(8-trifluoromethyl-4-quinolyl)-anthranilic acid sodium salt, 4.98 g of 90% 3-(β-chloroethyl)-oxazolidin-2-one and 60 ml of dimethylformamide was heated under stirring at 120° C. for five hours. Upon completion of the reaction, the mixture was cooled, filtered, and poured into 300 ml of water. The crude product was extracted with ethyl acetate, the solvent evaporated off and the residue crystallized from ethanol to give 6 g of N-(8-trifluoromethyl-4-quinolyl)-anthranilic acid β-(2-oxo-3-oxazolidinyl)-ethyl ester, melting at 158°–160° C.

EXAMPLE 4

A mixture comprising 10.62 g of N-(8-trifluoromethyl-4-quinolyl)-anthranilic acid sodium salt and 4.92 g of 3-bromo-oxolan-2-one in 60 ml of dimethylformamide was heated under stirring at 80° C. for five hours. Upon completion of the reaction, the solution thus obtained was cooled, filtered and poured into 300 ml of water. The crude solid was extracted with ethyl acetate. The solvent was evaporated off and the residue crystallized from ethanol to give 7 g of N-(8-trifluoromethyl-4-quinolyl)-anthranilic acid γ-butyrolactone ester, melting at 168°–169° C.

EXAMPLE 5

A mixture comprising 10.62 g of N-(7-trifluoromethyl-4-quinolyl)-anthranilic acid sodium salt, 4.98 g of 90% 3-(β-chloroethyl)-oxazolidin-2-one and 60 ml of dimethylformamide was heated under stirring at 120° C. for five hours. Upon completion of the reaction, the mixture was cooled, insoluble sodium chloride was filtered off, and the solvent was evaporated off in vacuo. The residue was treated with 200 ml of water and the solid, collected by filtration, crystallized from methylene dichloride: petroleum ether. 8.7 g of N-(7-trifluoromethyl-4-quinolyl)-anthranilic acid β-(2-oxo-3-oxazolidinyl)-ethyl ester, melting at 124°–125° C., were obtained.

EXAMPLE 6

A mixture comprising 10.62 g of N-(7-trifluoromethyl-4-quinolyl)-anthranilic acid sodium salt, 3.24 ml of 3-bromo-oxolan-2-one and 60 ml of dimethylformamide was heated under stirring at 80° C. for five hours. Upon completion of the reaction, the mixture was cooled, the insoluble sodium bromide was filtered off, and the solvent was evaporated off in vacuo. The residue was treated with 200 ml of water, the solid collected and crystallized from ethanol to give 7.7 g of N-(7-trifluoromethyl-4-quinolyl)-anthranilic acid γ-butyrolactone ester, melting 183°–184° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. An anthranilic acid derivative having the structural formula (I):

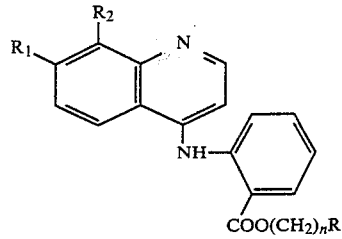

wherein n is 0, 1 or 2, one of $R_1$ and $R_2$ is chloro or trifluoromethyl and the other is hydrogen, and R is 2-oxo-3-oxolanyl or 2-oxo-3-oxazolidinyl.

2. The derivative as defined by claim 1, the same being N-(7-chloro-4-quinolyl)-anthranilic acid γ-butyrolactone ester.

3. The derivative as defined by claim 1, the same being N-(7-chloro-4-quinolyl)-anthranilic acid β-(2oxo-3-oxazolidinyl)-ethyl ester.

4. The derivative as defined by claim 1, the same being N-(8-trifluoromethyl-4-quinolyl)-anthranilic acid β-(2-oxo-3-oxazolidinyl)-ethyl ester.

5. The derivative as defined by claim 1, the same being N-(8-trifluoromethyl-4-quinolyl)-anthranilic acid γ-butyrolactone ester.

6. The derivative as defined by claim 1, the same being N-(7-trifluoromethyl-4-quinolyl)-anthranilic acid β-(2-oxo-3-oxazolidinyl)-ethyl ester.

7. The derivative as defined by claim 1, the same being N-(7-trifluoromethyl-4-quinolyl)-anthranilic acid γ-butyrolactone ester.

8. A pharmaceutical composition of matter comprising an analgesically or anti-inflammatory effective amount of the anthranilic acid derivative as defined by any of claims 1 to 7, and a pharmaceutically effective diluent or carrier therefor.

9. The method for eliciting an analgesic or anti-inflammatory response in a warm-blooded animal, comprising administering to a warm-blooded animal in need of such treatment, an analgesically or anti-inflammatory effective amount of the anthranilic acid derivative as defined by any of claims 1 to 7.

10. The method for eliciting an analgesic or anti-inflammatory response in a warm-blooded animal, comprising administering to a warm-blooded animal in need of such treatment, the pharmaceutical composition of matter as defined by claim 8.

* * * * *